United States Patent [19]
Frater et al.

[11] Patent Number: 5,902,312
[45] Date of Patent: May 11, 1999

[54] SYSTEM FOR MOUNTING BOLSTER MATERIAL ON TISSUE STAPLERS

[76] Inventors: Dirk A. Frater, 4300 Versailles Ave., Dallas, Tex. 75205; Robert W. M. Frater, 17 Gladwin Pl., Bronxville, N.Y. 10708

[21] Appl. No.: 08/981,880

[22] PCT Filed: Jul. 2, 1996

[86] PCT No.: PCT/US96/11350

§ 371 Date: Mar. 24, 1998

§ 102(e) Date: Mar. 24, 1998

[87] PCT Pub. No.: WO97/01989

PCT Pub. Date: Jan. 23, 1997

Related U.S. Application Data

[60] Provisional application No. 60/000,855, Jul. 3, 1995, and provisional application No. 60/014,435, Mar. 29, 1996.

[51] Int. Cl.[6] ........................................................ A61F 2/02
[52] U.S. Cl. ................................................................ 606/148
[58] Field of Search ................................... 606/139, 140, 606/144, 145, 146, 147, 148, 219, 220, 142, 143, 151, 1; 128/898; 227/178–182, 19, 901; 623/2

[56] References Cited

U.S. PATENT DOCUMENTS

| 5,133,723 | 7/1992 | Li et al. ............................. 606/139 X |
| 5,141,144 | 8/1992 | Foslien et al. . |
| 5,263,629 | 11/1993 | Trumbull et al. . |
| 5,405,352 | 4/1995 | Weston ............................... 606/139 X |
| 5,503,638 | 4/1996 | Cooper et al. ......................... 606/148 |
| 5,542,594 | 8/1996 | McKean et al. ..................... 227/178.1 |

*Primary Examiner*—Michael Buiz
*Assistant Examiner*—Vikki Trinh
*Attorney, Agent, or Firm*—Trexler, Bushnell, Giangiorgi & Blackstone, Ltd.

[57] ABSTRACT

A bolster assembly (1, 5; 110) for mounting upon a surgical stapler instrument (7, 120) to prevent displacement of activated staple from the stapled tissue (9, 129), includes a tissue reinforcing or bolster material (1, 112) secured to a carriage and support structure (5, 116) which facilitates the mounting of the bolster material (1, 112) on the stapler, in which the bolster material (1, 112) is removably fastened to the support structure (5, 116) by a single length (2, 122) of continuous filament, in order to facilitate removal of the filament and unfastening of the bolster material (1, 112) from the support structure (5, 116).

10 Claims, 5 Drawing Sheets

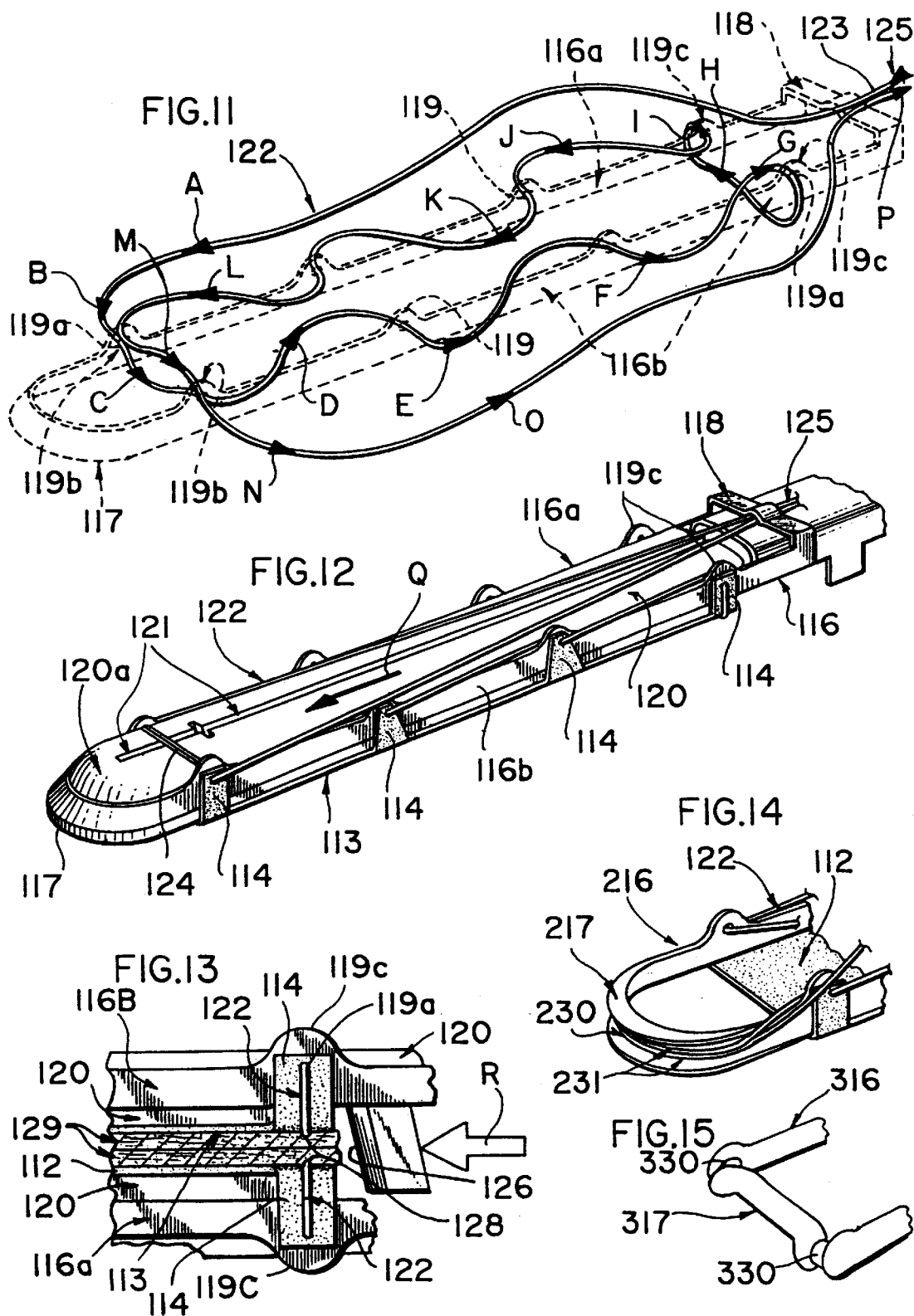

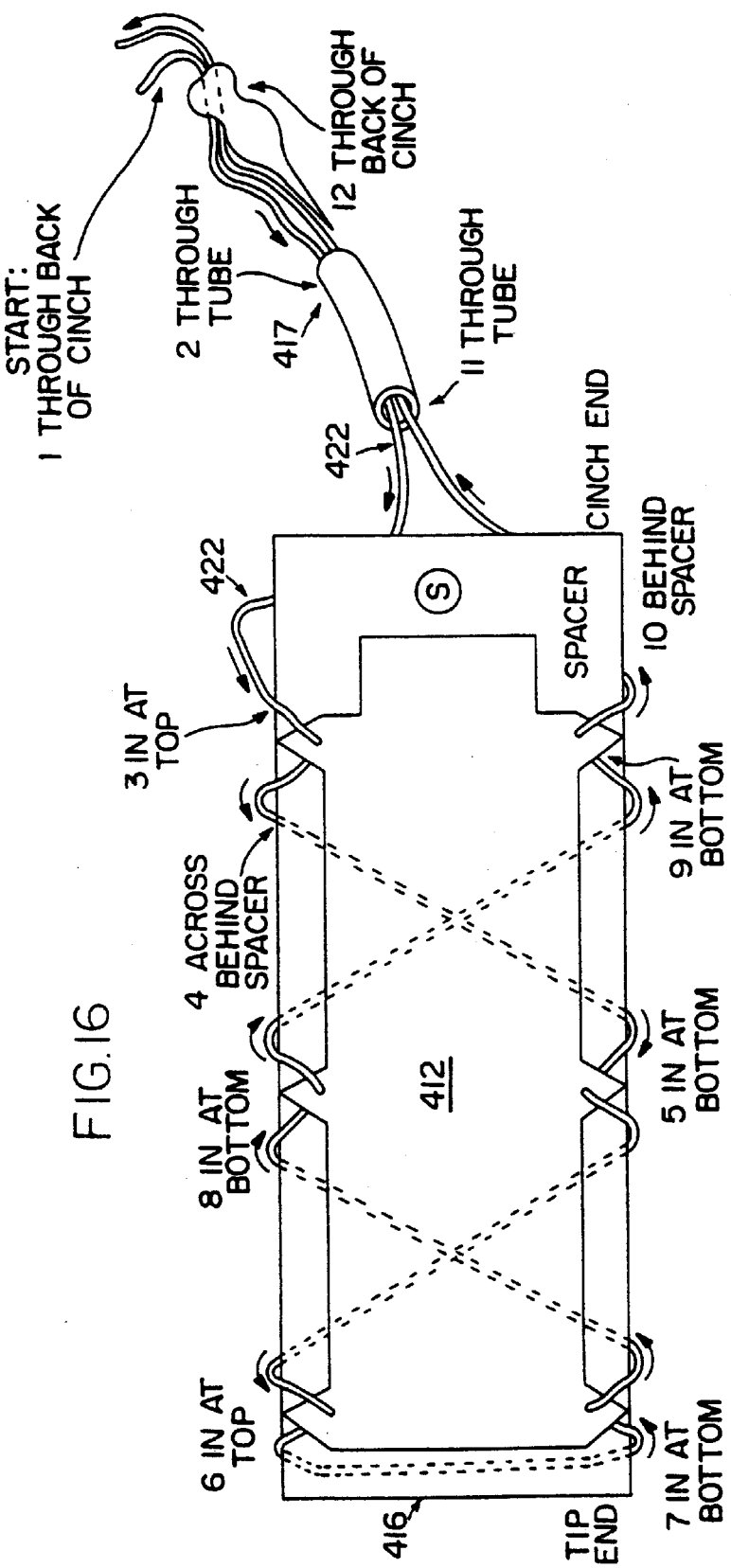

SYSTEM FOR MOUNTING BOLSTER MATERIAL ON TISSUE STAPLERS

REFERENCE TO RELATED APPLICATIONS

This application is a National Phase application based upon application Ser. No. PCT/US 96/11350, International Filing Date: Jul. 2, 1996, entitled: SYSTEM FOR MOUNTING BOLSTER MATERIAL ON TISSUE STAPLERS. In addition, this application is also a continuation-in-part of U.S. Provisional Applications: 1) Ser. No. 60/000,855, filed: Jul. 3, 1995, entitled: SYSTEM FOR MOUNTING PERICARDIAL BOLSTERS ON TISSUE STAPLERS and 2) Ser. No. 60/014,435, filed: Mar. 29, 1996, entitled: MOUNTING SYSTEM FOR STAPLE BOLSTERS. Copendency having been established by the filing of said PCT application and full benefits with respect to the filing dates of the earlier applications under 35 USC 120 are herewith claimed.

BACKGROUND

This Application relates generally to surgical stapling procedures and instruments, and more particularly relates to improvement in devices mounted on the stapler to reinforce the staple line, especially beneficial in endoscopic procedures.

When staples are applied to fragile tissue, particularly fragile emphysematous lung in the course of lung volume reduction surgery, there is a very real danger of tearing of the tissue with consequent leaking of air. When this happens the patient is put at serious risk of a prolonged hospitalization, potential reoperation and even mortality. The solution to this problem has been to use a strip of material mounted on the anvil and the cartridge arms of the stapler so that when the staples are fired the tissue is compressed between two layers of material that is itself much stronger than the lung tissue. The material must be thin enough for the staples to close over the sandwich of membrane and compressed tissue, strong enough for there to be no risk that staples could possibly tear through it and biocompatible so that it may be left in the body without producing excessive host reactions. The material most used has been tanned bovine pericardium, but permanent or slowly absorbable synthetic materials with proven effectiveness as patch materials in other parts of the body such as extruded polytetrafluorethylene, polyester, polypropylene, vicryl, dexon can all be used provided they are thin enough and strong enough.

The bolster material may be hand cut and tied to the stapler arms. It is far more conveniently supplied sterile, precut, and with a mounting mechanism that enables it to be easily placed on the stapler, and remain secure there while the stapler is maneuvered onto the tissue. For endoscopic use in which the stapler is passed through the body wall, the mounted bolster must not be displaced during this maneuver. Ideally, the removal of the mounting mechanism must be easily and routinely accomplished with a minimum of maneuvers and time. A currently available product as described in U.S. Pat. No. 5,503,638 has pericardium attached by sutures to a rectangular polyethylene three sided box that fits over the staple arm. For removal the sutures need to be cut at least twice and sometimes four times for release of the mounting mechanism. Access to the sutures may require twisting or rotating the stapler from side to side. In endoscopic use, particularly, the torque thereby applied to the delicate adjacent lung tissue outside the staple line may cause tears to occur so that the beneficial effect of the bolstering of the staples is lost. After the removal of the sutures, the polyethylene "box" must also be removed.

These and other disadvantages are eliminated by bolster mounting assemblies in accordance with the present invention.

SUMMARY OF THE INVENTION

In accordance with the present invention, a bolster assembly for mounting upon a surgical stapler instrument to prevent displacement of activated staples from the stapled tissue, includes a tissue reinforcing or bolster material secured to a carriage and support structure which facilitates the mounting of the bolster material on the stapler, in which the bolster material is removably fastened to the support structure by a single length of continuous filament, in order to facilitate removal of the filament and unfastening of the bolster material from the support structure. In at least two embodiments, the configuration of the removable fastening by the single length of continuous filament enables a single severing of the single filament length to produce two lengths arranged to allow joint removal thereof and convenience in unfastening the bolster material from the support structure.

In one embodiment, a pericardial bolster strip with a pre-mounted suture and a tube placed between the suture and the pericardium. The staple arm is loaded by simply pushing the nose cone of the arm into the tube and using it to push the tube out from between the suture and the bolster strip. The loading is completed by cinching up the suture with one hand and the operation is performed by one person in seconds. One size of pre-mounted bolster strip fits both the cartridge and the anvil arms of the stapler. Once the staples have been fired the suture is removed with one pull after cutting it once, preferably at one of the ends.

The simplest and cheapest way to secure bolster strip to staplers is with sutures: the disadvantage of this method is that it takes time and since it must be done in the operating room prolongs the operation and anesthetic time inappropriately. This invention completely removes that delay and thus provides an efficient way of using the simplest and least expensive method of mounting pericardium on staplers.

Finally, the method employs somewhat more bolster strip than the method that uses a polyethylene sheath; as a result of this there is enough bolster strip behind the staple line for another line of staples to be laid down if there is any question about residual air leaks.

In another embodiment of the bolster mounting assembly, the support structure includes a pair of spaced elongate members, each having a plurality of lateral lug portions to which respective flaps of the reinforcing material strip are fastened by the single length of continuous filament. The continuous filament extends along at least one of the elongate members and passes therefrom to the other of the elongate members so that all of the bolster flaps and body are anchored on the support structure by the same continuous filament.

BRIEF DESCRIPTION OF THE DRAWINGS

FIG. 11 is a perspective view of the suture path by which the suture progressively passes along and through the bracket shown in hidden line in fastening the bolster strip which has been omitted for clarity in viewing the suture path;

FIG. 12 is a perspective view of the bolster mounting assembly of FIGS. 9 and 10 fully mounted onto the stapler arm;

FIG. 13 is a fragmentary, side view of two stapler arms with respective bolster mounting assemblies thereon showing tissue stapled therebetween in readiness for cutting of both tissue layers, bolster strips and sutures in a single motion of a knife member on the stapler;

FIG. 14 is a fragmentary, perspective view of a third embodiment of a bolster mounting assembly in accordance with the invention showing a support bracket groove for guiding removal of the suture;

FIG. 15 is a fragmentary, perspective view of a fourth embodiment of a bolster support bracket in accordance with the invention showing plural bracket grooves for guiding removal of the suture; and FIG. 16 is a plan view of a fifth embodiment of a bolster mounting assembly in accordance with the invention.

DETAILED DESCRIPTION OF THE ILLUSTRATED EMBODIMENTS OF THE INVENTION

Figure 1:
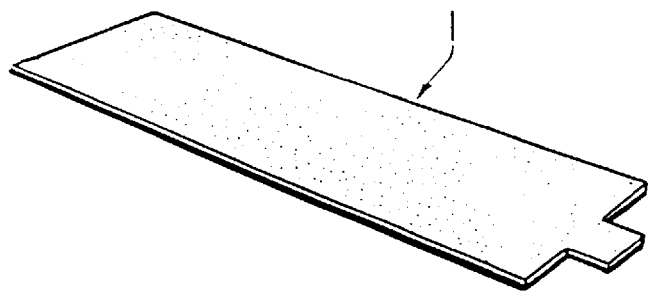
FIG. 1 is a perspective view of a bolster panel or strip incorporated in a first embodiment of a mounting assembly in accordance with the present invention.

Referring to FIG. 1, a biocompatible bolster panel or strip 1 is cut to appropriate configuration suited to the particular stapler arm on which the bolster strip 1 is to be employed as described hereinafter.

Figure 2:
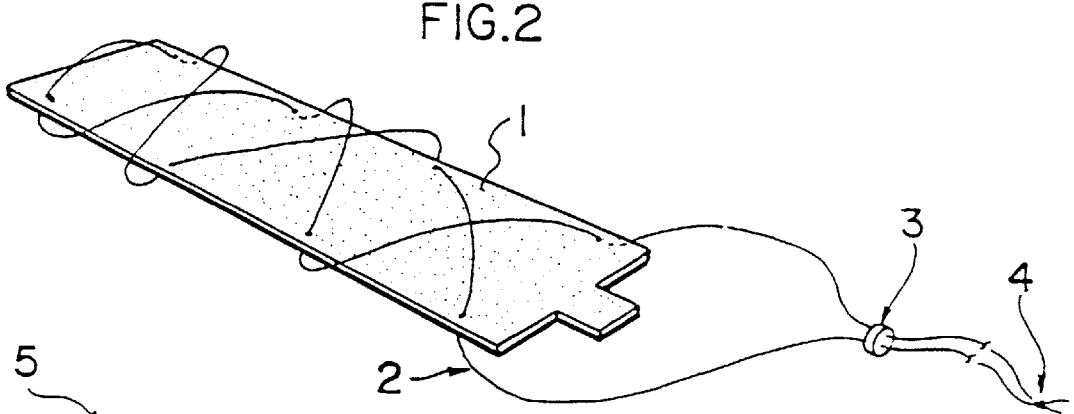
FIG. 2 is a perspective view of the bolster strip shown in FIG. 1 through which a continuous length of suture has been woven with obliquely extending portions.

Referring to FIG. 2, the continuous suture 2 is passed through the bolster strip 1 from the proximal end of the bolster strip 1, in the proper pattern to enable it to be secured to the stapler, down to the distal end and back again to the base. Both ends of the suture are then passed through a cinch 3, finally the ends are knotted, leaving a variable length of the two ends 4, dependent on the use to which the stapler is being put. For endoscopic applications the ends are long enough to be brought through the trochar so that as they are pulled out they can be removed in one movement with the stapler.

Figure 3:
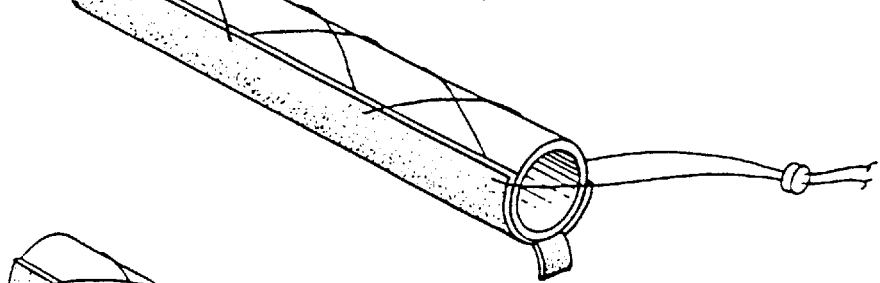
FIG. 3 is perspective view of the bolster strip of FIG. 2 secured by the suture upon a tubular support structure in accordance with a first embodiment of the present invention.

Referring to FIG. 3, a tube 5 is placed between the bolster strip 1 and the suture, and keeps them apart. The size and length of the tube depends on the particular stapler that is being loaded. It is a feature of the method that some differences in dimensions (e.g. between anvil and cartridge of some staplers) can be handled by one size of tube.

Figure 4:
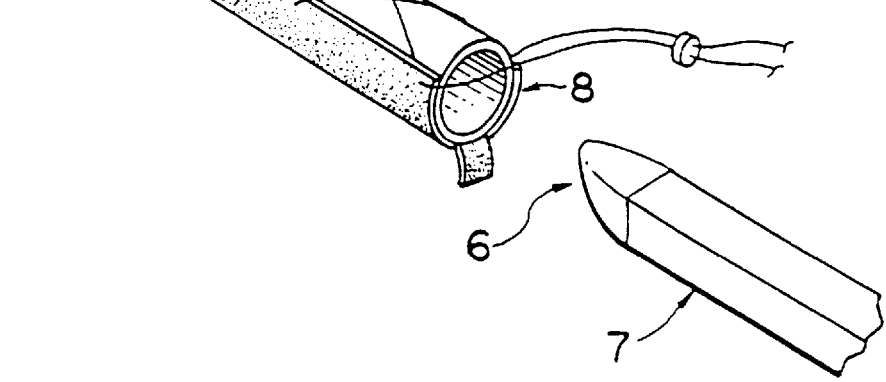
FIG. 4 is a perspective view of the assembly of FIG. 3 in preparation form mounting thereof on a stapler arm.

Referring to FIG. 4, the nose cone 6 of an arm of a stapler 7 is about to be passed into the hollow end of the proximal end 8 of the assembled bolster strip-suture-tube combination.

Figure 5:
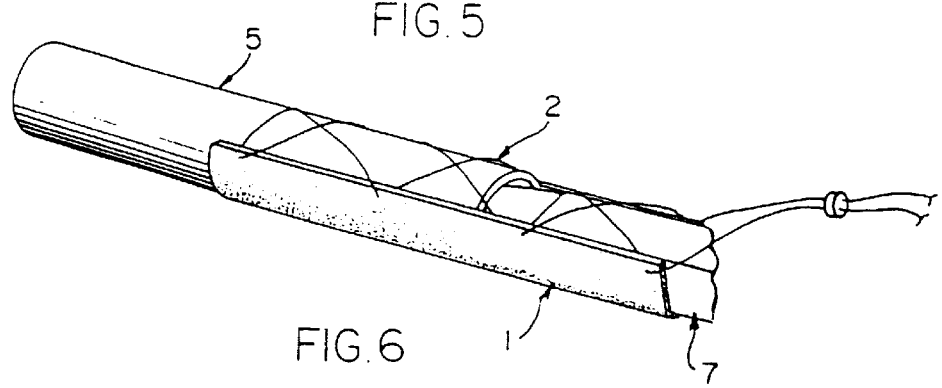
FIG. 5 is a perspective view of the mounted assembly on the stapler arm of FIG. 4 showing initiation of the dismounting of only the tubular support structure.

Referring to FIG. 5, as the staple arm 7 is used to push the tube 5 out from between the pericardium 1 and the suture 2, the bolster strip 1 and suture are automatically brought into position on the stapler.

Figure 6:
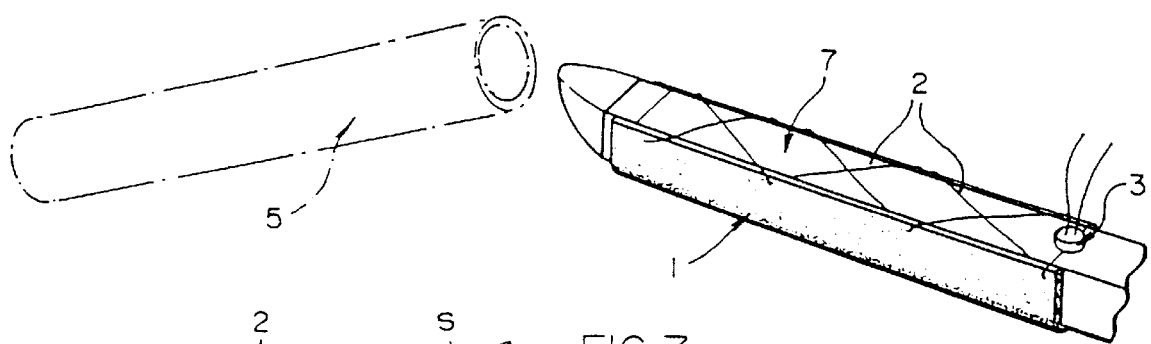
FIG. 6 is a perspective view of the fully dismounted tubular support structure of FIG. 5.

Referring to FIG. 6, the tube 5 has been discarded, and the suture 2 tightened by means of the cinch 3. The strip 1 is held securely on the staple arm, ready to act as a bolster when the stapler is fired.

Figure 7:
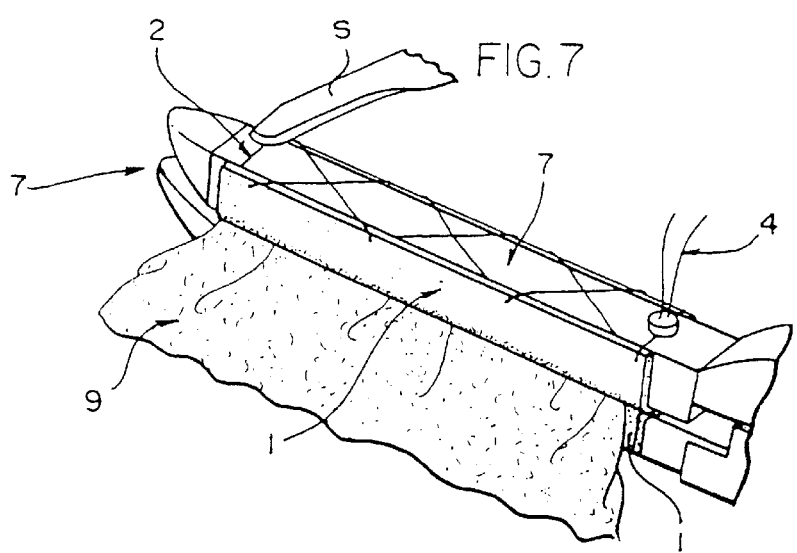
FIG. 7 is perspective view of two arms of the stapler with mounted bolster assemblies and removed tubular support structures according to FIG. 6, further showing lung tissue to be stapled.

Referring to FIG. 7, the two arms of the stapler 7,7 both loaded with strip 1 have been applied together to the lung 9 which is compressed between a layer of strip 1 on each side. The suture 2 is about to be cut by scalpel S so that the knotted end of the suture 4 can be pulled to remove the whole suture.

Figure 8:
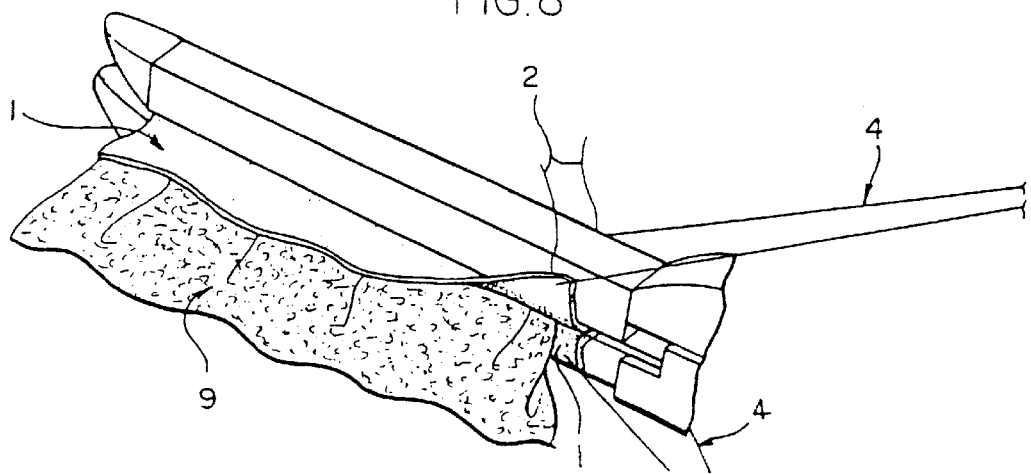
FIG. 8 is a perspective view similar to FIG. 7 showing the lung tissue stapled through the bolster strips and further showing each of the severed continuous sutures being removed.

Referring to FIG. 8, the ends of the cut suture 2 have been almost completely removed by pulling on the knotted end 4. The bolster strip 1 that was held against the sides of the stapler arms now falls back against the lung, where it is available to buttress extra staples, if they are needed.

Figure 9:
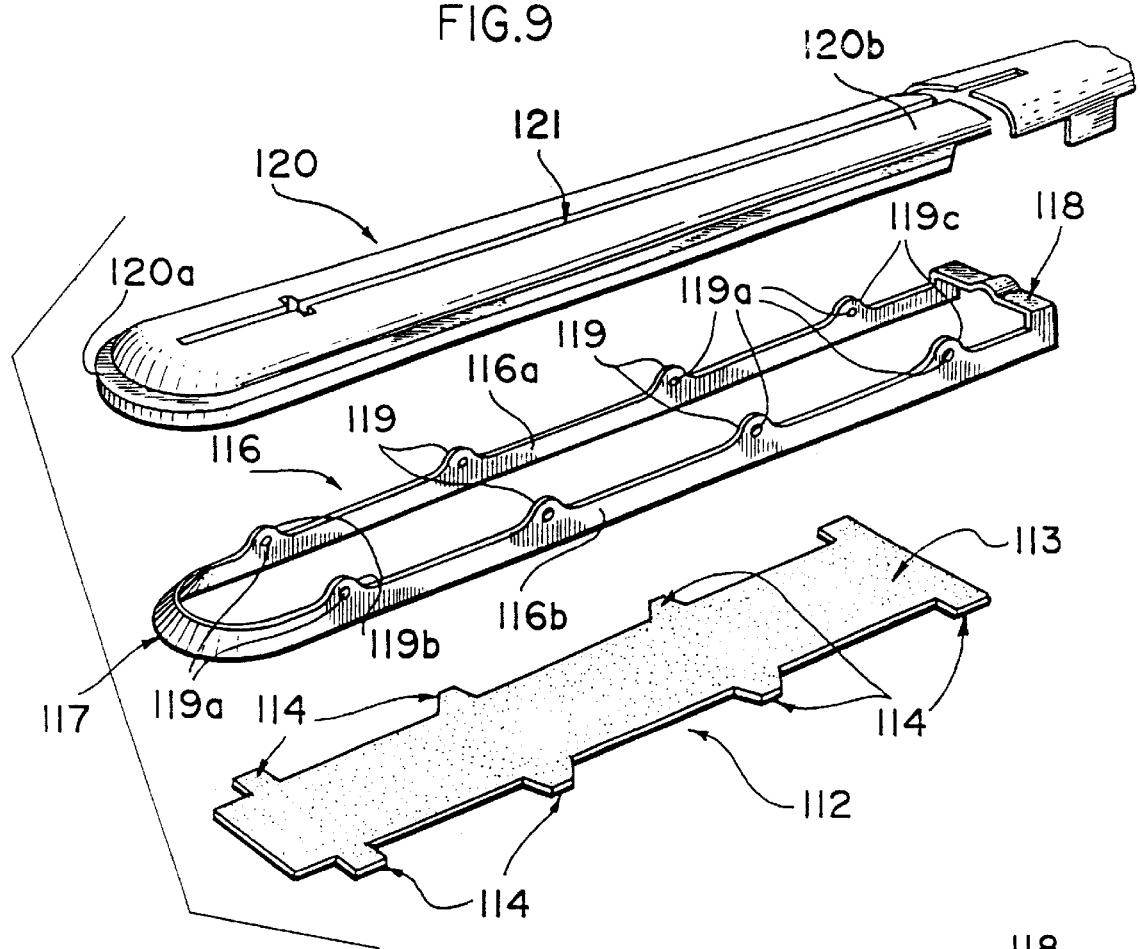
FIG. 9 is an exploded, perspective view of a second embodiment of a bolster mounting assembly in accordance with the invention, and a corresponding stapler arm.
Figure 10:
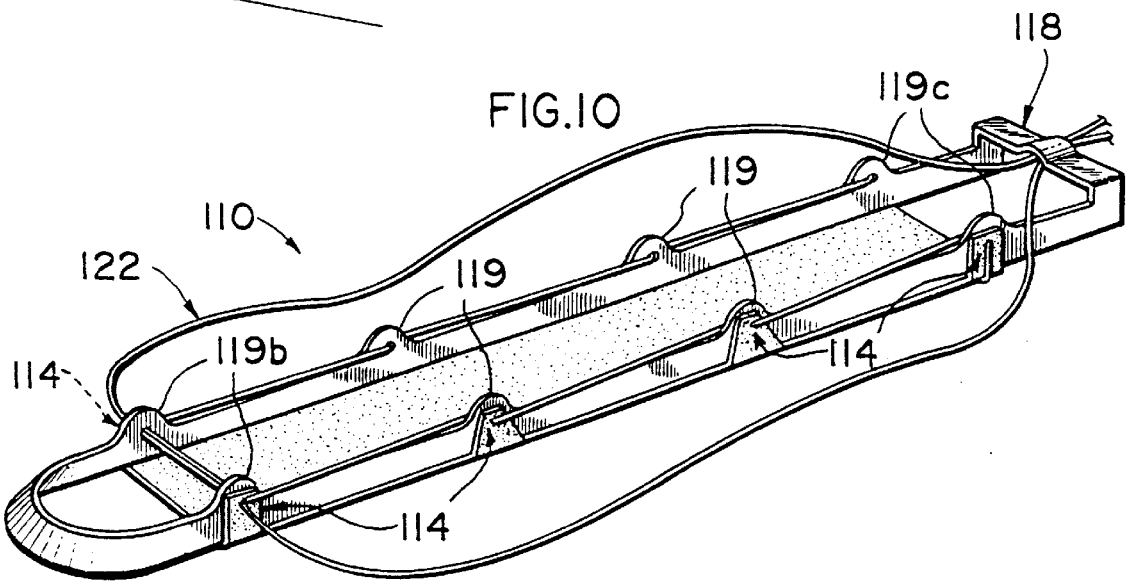
FIG. 10 is a perspective view of the bolster strip and support bracket of FIG. 9 fastened with a continuous suture.

Referring now to FIGS. 9 and 10, a second embodiment of the staple bolster assembly for tissue staplers in accordance with the present invention, is designated generally by a reference character 110. Referring particularly to FIG. 9, a biocompatible bolster strip 112 is fabricated with a series of laterally extending, anchoring flaps 114 in the illustrated embodiment. The bolster strip 112 is secured onto a support structure 116 which has two spaced longitudinal arms which are dimensioned to snugly fit on the respective outer sides of a typical tissue stapler arm 120 in any of a variety of stapler configurations, preferably of the tissue cutting type, for example the "Auto Suture™" line of disposal surgical staplers marketed by United States Surgical Corporation and particularly the MULTIFIRE GIA disposal stapler suited to endoscopic procedures. In the particular configuration illustrated, the ends of the bracket arms 116a and 116b are joined by a forward, distal end bridge 117 as well as a rear or proximal end bridge 118 shaped for accommodation on the stapler arm 120.

The bolster strip 112 is secured on the support structure bracket 116 by attaching the anchoring flaps 114 to respective anchoring lugs 119 extending from the bracket arms 116a and 116b. The initial alignment of the flaps 114 with the lugs 119 locates the elongate body panel 113 of the strip 112 for proper positioning and extension on the bracket 116 as shown in FIG. 10. The anchoring flaps 114 of the bolster strip 112 are secured to the bracket lugs 119 by a continuous suture strand 122 which is tensioned to hold the bolster flaps against the respective arms. The continuous suture strand 122 as shown in FIG. 10, enables the suture to be conveniently removed as a unit following the stapling operation as more fully described. Securement of the bolster strip 112 and flaps 114 is achieved by progressively threading the suture strand 122 through the flaps, and preferably through the lugs 119 and respective holes 119a along a suitable path to allow a minimum of severings of the suture strand for swift release and removal.

One particularly suitable suture path is shown in FIG. 11 from which the bolster strip 112 has been omitted (in contrast to FIG. 10) for clarity in viewing the suture path. In the illustrated suture path of FIG. 11, the suture strand end portion 123 is initially fed under the proximal end bridge 118 in the direction of arrowhead A through one of the lugs 119*b* most adjacent to the distal bridge 117 of the bracket which will later be mounted nearest the front end 120*a* of the stapler arm 120 (as shown in FIG. 9). In FIG. 11, the initial feed of the suture strand 123 through one of the distal end lugs 119*b* is shown in the direction of arrowhead B indicating that the suture has been passed firstly to penetrate the flap 114 and then through the lug hole 119*a* from the exterior side of the end lug 119*b* inwardly, then passes directly across the bracket toward the arm 116*b* and the distal end lug 119*b* transversely opposite the first end lug 119*b* as indicated in the direction of the arrowhead C (as also shown in FIG. 10). From the arrowhead C, the suture then passes from the interior of the opposite lug 119*b* through hole 119*a* (to penetrate the aligned flap 114 as shown in FIGS. 10 and 12) and then jogs inwardly as indicated by arrowhead D to the interior of the next adjacent lug 119 through which the suture passes outwardly (and then penetrates the aligned flap 114) in the direction of arrowhead E. Thereafter, the suture again jogs inwardly to the next adjacent lug 119*e* and passes from the interior thereof outwardly (penetrating the adjacent flap, as in FIGS. 10 and 12 in the direction of arrowhead F before again jogging inwardly to the interior side of the adjacent, distal end lug 119*c* most adjacent to the distal bracket bridge 118 which will later be mounted nearest the rear or handle end 120*b* of the stapler arm 120 (as shown in FIG. 9). As indicated by the direction of arrowhead G, the suture then passes through the lug hole 119*a* from the interior side of lug 119*b* outwardly, so that it then penetrates the aligned flap 114 (as shown in FIGS. 10 and 13). Emerging outwardly from the lug 119*c* (and flap 114), the suture then passes around the bracket arm 116*b* (and strip body 113 shown in FIG. 13), and then directly across the bracket in the direction of arrowhead H toward the arm 116*a* and the proximal end lug 119*c* transversely opposite the first end lug 119*c*. From the direction of arrowhead H, the strand passes around the arm 116*a* to the exterior side of the lug 119*c* (then penetrates the aligned flap 114) and continues inwardly through the hole 119*a* of the lug I 19*c* to the interior side of the lug 119*c* in the direction of the arrowhead I. From the direction of the arrowhead I, the suture then jogs outwardly in the direction of arrowhead J to the exterior side of the next adjacent lug 119 (where it penetrates the aligned flap 114) before passing through hole 119*a* to the interior side thereof in the direction of arrowhead K before again jogging outwardly to the next adjacent lug 119 passing therethrough outwardly to inwardly and continuing in the direction of arrowhead L to the exterior side of the next adjacent, distal end lug 119*b* before passing outwardly to inwardly through the hole 119*a* through which the suture has previously passed along arrowhead B so that the suture forms a double strand in passing along the arrowhead M directly across and through the transversely opposite end lug 119*b* emerging from inwardly to outwardly in the direction of the arrowhead N.

From the direction of arrowhead N, the suture returns along the direction indicated by arrowhead 0 to pass under the proximal bracket end bridge 118 under which the suture was initially fed so that the suture forms a double strand of operating leads 125 which are then pulled to tension the continuous suture 122 so that the tension in the suture draws and firmly seats each of the bolster strip flaps 114 against the respective bracket arms 116*a*, 116*b* and lugs 119, which properly positions the bolster strip body 113 on the bracket 116. The suture tension can be maintained by knotting or cinching the double suture strand 125 against the bridge 118, or in any other suitable manner. The double suture strand 125 can extend rearwardly in variable lengths suited to the stapler arm on which the bolster strip and bracket are to be mounted and the surgical procedure to be performed. For endoscopic procedures, the double strand 125 is extended long enough to be brought through a trochar or endoscope. Once the suture 122 has been properly tensioned, the appropriate stapler arm 120 can be inserted so that its front end 120*a* enters the bracket 116 passing beneath the bridge 118 and slides in the direction of arrowhead Q to seat against the distal bracket end 117 as shown in FIG. 12.

In the illustrated embodiment of FIGS. 12 and 13, one of the stapler arms 120,120 is provided with a conventional, longitudinally moveable cutting edge 126 which is arranged for motion along the arms 120,120 in the direction of the arrowhead R. After two of the stapler arms 120,120 have been loaded with the bolster strip/bracket assemblies as shown in FIGS. 10 and 12, and the stapler arms have been applied together in a manner similar to FIGS. 7 and 8, the staples can be fired through both of the bolster strips 112,112 to join the subject tissues 129,129. Thereafter, the knife edge 126 can be moved in the direction of arrowhead R, (by the conventional, extended manual knife handle (not shown) on the stapler) so that the suture strand length 128 which extends beneath the two proximal end bracket lugs 119*c* as shown in FIG. 13, which was originally created at the location of the arrowhead H in FIG. 11, will be severed, and with continued motion of the cutting edge 126 through the stapler arm grooves 121. As a result, since the bolster strips 112,112 on the two stapler arms 120,120 have been stapled through in substantially back-to-back relationship, the two transverse strands 128,128 (which need not be aligned) on the respective stapler arms 120,120 can be severed in a single stroke of the cutting edge 126. The two severed transverse suture strands 128,128 release the four severed suture lengths 122 to be pulled from the two sets of double strands 125 at the proximal or rear end of the stapler so that the suture strands pass through the lug holes 119 and disengage from the multiple bolster flaps 114 in a single, convenient removal motion which also releases the bolster strips 112,112 from the brackets 116,116 leaving the supportive bolster strips 112,112 with the stapled tissue 129,129 and allowing the two brackets 116,116 to be withdrawn with the stapler arms 120,120 without any separate bracket removal complication.

Referring now to FIG. 14, a third embodiment of the bracket 216 is provided with an exterior, arcuate guide channel or groove 230 formed in the forward or distal bridge portion 217. In mounting the bolster strip 112, the continuous suture 122 will be passed around and through the guide channel 230 twice forming portions 231,231 in substitution for the two transverse paths forming the double strand 124 in FIG. 12. The guide channel 230 provides a curved path of release when the suture 122 is pulled rearwardly following severing of the suture length 122 for removal.

As shown in FIG. 15, a fourth embodiment of the bracket 316 includes a distal bridge portion 317 provided with two corner guide grooves 330,330 to provide two curved suture pathways for smoothing the release and removal of the severed suture strand (not shown) in substitution for the guide channel 230 shown in FIG. 14.

Referring now to FIG. 16, a fifth embodiment of a staple bolster assembly 410 is shown, in which a flat flexible spacer panel 416, for example rectangular plastic sheet, serves as the support structure. The bolster strip 412 is positioned on one side of the panel spacer 416 and the suture 422 is passed alternately through the bolster 412 and around the spacer 416. The ends of the suture are passed through a cinch 417 consisting of a silicone rubber tube and a tapered polyethelene obturator with a hole at the back end. The two suture ends are passed first through the tube and then through the back end of the obturator and is then threaded for example along the path illustrated. When the obturator is passed into the tube, the suture is squeezed between the tube wall and the obturator. The more the obturator is pushed into the tube, the more tightly the suture is held.

The bolster is loaded onto the stapler arm by passing the nose end of the arm between the pericardium and the spacer, with the stapling surface against the pericardium. Once the pericardium is properly aligned with the stapling surface of the staple arm, the spacer is pulled out and the suture is tightened and locked in position with the cinch. When the staples have been fired, the transverse stitches at the nose end of the anvil and cartridge arms are cut and the sutures are pulled out. With this design, one cut and one pull removes the mounting apparatus.

While a preferred embodiment of the present invention is shown and described, it is envisioned that those skilled in the art may devise various modifications and equivalents without departing from the spirit and scope of the appended claims.

The invention claimed is:

1. An assembly (1,5; 110) for mounting upon a surgical stapler instrument (7,120) and preventing displacement of activated staples from stapled tissue (9,129) comprising: a carriage and support structure (5,116), a tissue reinforcing material (1,112) having a proximal end, a distal end and first and second side edges, said tissue reinforcing material being removably secured to said carriage and support structure (5,116) to facilitate mounting the reinforcing material (1,112) upon the surgical stapler instrument (7,120), and a single length (2,122) of continuous filament connected proximate to said first and second side edges and between said first and second side edges for removably fastening the reinforcing material (1,112) to the support structure (5,116) in order to facilitate removal of the filament and unfastening of the reinforcing material (1,112) from the support structure (5,116).

2. An assembly according to claim 1, wherein said single length (2,122) of continuous filament can be severed to produce two lengths therefrom in arrangement allowing joint (4,125) removal thereof for the unfastening of said tissue reinforcing material from said carriage and support structure.

3. An assembly according to claim 1, wherein a configuration of said single length (122) of continuous filament in the said removable fastening includes two generally parallel portions (J,K,L;D,E,F) and a transverse portion (H) extending transversely between said parallel portions.

4. An assembly according to claim 1, wherein said support structure (5) comprises a cylindrical tube (5) through which a portion (7) of said surgical stapler instrument is insertable in mounting said assembly thereon.

5. An assembly according to claim 1, wherein said support structure (116) includes a plurality of extending lug portions (119) to which a respective plurality of flap portions (114) of said reinforcing material (112) are fastened by said single length (122) of continuous filament.

6. An assembly according to claim 5, wherein one or more of said extending lug portions (119) includes an aperture (119a) through which said single length of continuous filament passes in fastening said respective flap (114).

7. An assembly according to claim 1, wherein said support structure (116) includes a pair of spaced, elongate members (116a, 116b) between which a transverse portion (H) of said single length (122) of continuous filament extends transversely therebetween.

8. An assembly according to claim 1, wherein said support structure includes a spaced pair of elongate members (116a, 116b) and a configuration of said single length (122) of continuous filament extends along one of said elongate members and includes at least one passage portion (C,H,M) therefrom extending to the other of said elongate members.

9. An assembly according to claim 1, wherein said support structure (116) includes a spaced pair of elongate members (116a, 116b) which are joined on at least one pair of respective ends thereof by a bridge portion (117,118).

10. An assembly according to claim 1, wherein said support structure (5) is slidably removable from said tissue reinforcing material and said single length of continuous filament length (2) remains.

* * * * *

UNITED STATES PATENT AND TRADEMARK OFFICE
CERTIFICATE OF CORRECTION

PATENT NO. : 5,902,312
DATED : May 11, 1999
INVENTOR(S) : Dirk A. Frater and Robert W.M. Frater It is certified that error appears in the above-identified patent and that said Letters Patent is hereby corrected as shown below:

Column 8, Line 41 "filament length (2) remains."
should be -- filament. --

Signed and Sealed this

Fifteenth Day of August, 2000

Attest:

Q. TODD DICKINSON

Attesting Officer

Director of Patents and Trademarks